United States Patent
Kano et al.

(10) Patent No.: US 6,794,519 B2
(45) Date of Patent: Sep. 21, 2004

(54) PROCESS FOR THE PRODUCTION OF SULFONIC ESTERS

(75) Inventors: Fumihiko Kano, Himeji (JP); Shigeki Kunihiro, Kanzaki-gun (JP); Noritaka Yoshida, Matsubara (JP); Natsuki Mori, Kakogawa (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 10/067,784

(22) Filed: Feb. 8, 2002

(65) Prior Publication Data

US 2003/0162966 A1 Aug. 28, 2003

(51) Int. Cl.$^7$ ...................... C07D 207/04; C07C 303/26
(52) U.S. Cl. ......................... 548/541; 548/556; 558/44
(58) Field of Search ............................... 548/541, 556; 558/44

(56) References Cited

FOREIGN PATENT DOCUMENTS

| JP | 61-207370 | 9/1986 | |
|---|---|---|---|
| JP | 62-240651 | 10/1987 | |
| JP | 1-143852 | 6/1989 | |
| JP | 4-25946 | 5/1992 | |
| JP | 9-202763 | 8/1997 | |
| WO | WO 01/94304 A1 | 12/2001 | ......... C07C/309/65 |

OTHER PUBLICATIONS

Yamada Koichiro, et al., *Production of optically active 1–substituted–2–aminopropane*, Oct. 21, 1987, JP 62–240651.

Kutsuki Hidetoshi, et al., *Production of optically active 1–Benzyl–3–hydroxypyrrolidine*, Jun. 6, 1989, JP01–143852.

*Primary Examiner*—Joseph K. McKane
*Assistant Examiner*—Golam M M Shameem
(74) *Attorney, Agent, or Firm*—Kenyon & Kenyon

(57) ABSTRACT

Sulfonic acid ester derivatives represented by the general formula (4) or (5) are produced by reacting an amino alcohol derivative represented by the general formula (1) or (2) with an organic sulfonyl halide represented by the general formula (3), in a mixed solvent composed of an aprotic organic solvent and water in the presence of a non-water-prohibiting inorganic base. This procedure can be carried out in a simple, easy, safe and economical manner while reducing the load on the environment.

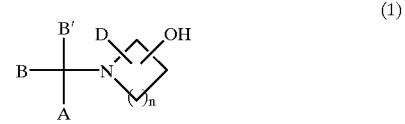

(1)

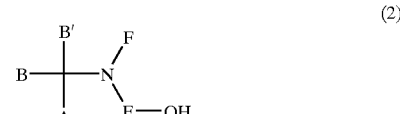

(2)

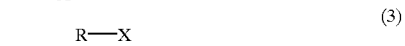

(3)

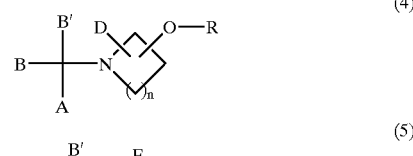

(4)

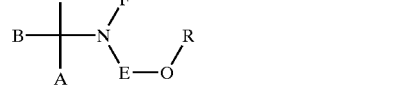

(5)

Wherein n represents an integer of 0 to 5, A represents a phenyl group, which may be substituted, R represents a methanesulfonyl, ethanesulfonyl, p-toluenesulfonyl or p-nitrobenzenesulfonyl group and X represents a chloride, bromine or iodine atom.

25 Claims, No Drawings

PROCESS FOR THE PRODUCTION OF SULFONIC ESTERS

CROSS REFERENCE TO RELATED APPLICATIONS

This application is a continuation of PCT/JP00/08277, filed Nov. 24, 2000, and claims priority to JP 2000-172509, filed Jun. 8, 2000.

TECHNICAL FIELD

The present invention relates to a method of producing sulfonic acid ester derivatives, which are useful as intermediates for the synthesis of fine chemicals such as medicinal compounds and agrochemicals, represented by the general formula (4):

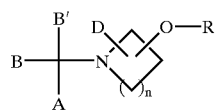

(4)

or the general formula (5):

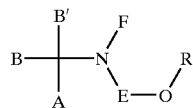

(5)

wherein n represents an integer of 0 to 5, A represents a phenyl group, which may be substituted, B and B' may be the same or different and each represents a phenyl group, which may be substituted, a straight or branched alkyl group containing 1 to 4 carbon atoms or a hydrogen atom, D represents a straight or branched alkyl group containing 1 to 8 carbon atoms, which may be substituted, or a hydrogen atom, E represents a straight or branched alkylene group containing 1 to 8 carbon atoms, which may be substituted, F represents a straight or branched alkyl group containing 1 to 8 carbon atoms, which may be substituted, and R represents a methanesulfonyl, ethanesulfonyl, p-toluenesulfonyl or p-nitrobenzenesulfonyl group.

BACKGROUND ART

Known in the art for producing sulfonic acid ester derivatives represented by the above general formula (4) or (5) are the method comprising reacting the corresponding amino alcohol derivative with an organic sulfonyl halide in an organic solvent in the presence of an organic base, for example a tertiary amine such as triethylamine or an aromatic amine such as pyridine, or in such an organic base; and the method comprising reacting the corresponding amino alcohol derivative with an organic sulfonyl halide in an anhydrous organic solvent in the presence of a water-prohibiting base such as sodium hydride or sodium amide.

Specifically, there are known the method comprising reacting 1-benzyl-3-pyrrolidinol with methanesulfonyl chloride or toluenesulfonyl chloride in the presence of an organic base such as triethylamine or pyridine (JP-A-07-116138; J. Med. Chem., 35 (1992) 22, 4205–4213) and the method comprising reacting 1-benzyl-3-pyrrolidinol with toluenesulfonyl chloride in an anhydrous solvent such as benzene or tetrahydrofuran in the presence of a water-prohibiting base such as sodium hydride or sodium amide (JP-A-51-125286; Laid-open European Pantent EP-0928787), among others.

However, these known production methods have the following problems, among others:

1) When an organic base such as a tertiary amine or an aromatic amine is used, the organic base is expensive. For isolating the sulfonic acid ester formed as an intermediate for the synthesis of fine chemicals such as medicinal compounds or agrochemicals, which are required to be of high quality, a high-level of purification for removal of the organic base, such as crystallization, distillation and/or column chromatography, is required (since the product sulfonic acid ester derivative itself is a kind of organic base, it is difficult to purify the same by such a simple technique as phase separation). The organic base is obtained as waste in an amount at least one equivalent relative to the product sulfonic acid ester derivatives.
2) When a water-prohibiting base, such as sodium hydride or sodium amide, is used, such water-prohibiting base itself is expensive. Such water-prohibiting base has a safe problem in handling in using it on a commercial scale.
3) In all the known methods, a high-level of purification, for example removal of the organic base by rectification, and/or dehydration, is required if the solvent is to be recovered and recycled. Such a purification process is economically difficult in many cases and the solvent is discharged as waste in increased amounts.

Thus, when evaluated as methods capable of reducing the load on the environment in the production of intermediates for high-quality fine chemicals such as medicinal compounds and agrochemicals on a commercial scale and in an economical manner, the prior art methods have problems.

In view of the state of the art as mentioned above, it is an object of the present invention to provide a method of economically producing the sulfonic acid ester derivatives represented by the general formula (4) or (5), which are intermediates for the synthesis of fine chemicals such as medicinal compounds or agrochemicals, which are required to be of high quality, in a simple and easy and safe manner while reducing the load on the environment.

DISCLOSURE OF INVENTION

The present invention thus provides a method of producing a sulfonic acid ester derivative represented by the general formula (4):

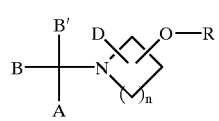

(4)

or the general formula (5):

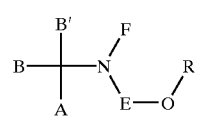

(5)

wherein n represents an integer of 0 to 5, A represents a phenyl group, which may be substituted, B and B' are the same or different and each represents a phenyl group, which may be substituted, a straight or branched alkyl group containing 1 to 4 carbon atoms or a hydrogen atom, D represents a straight or branched alkyl group containing 1 to 8 carbon atoms, which may be substituted, or a hydrogen atom, E represents a straight or branched alkylene group containing 1 to 8 carbon atoms, which may be substituted, F represents a straight or branched alkyl group containing 1 to 8 carbon atoms, which may be substituted and R represents a methanesulfonyl, ethanesulfonyl, p-toluenesulfonyl or p-nitrobenzenesulfonyl group, which comprises reacting an amino alcohol derivative represented by the general formula (1):

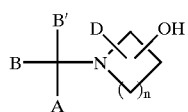

(1)

or the general formula (2):

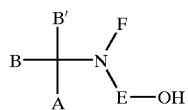

(2)

wherein n, A, B, B', D, E and F are as defined above, with an organic sulfonyl halide represented by the general formula (3):

R—X wherein R is as defined above and X represents a chlorine, bromine or iodine atom, in a mixed solvent composed of an aprotic organic solvent and water in the presence of a non-water-prohibiting inorganic base.

In the following, the present invention is described in detail.

The amino alcohol derivative represented by the general formula (1):

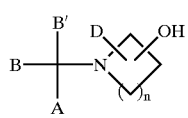

(1)

or the general formula (2):

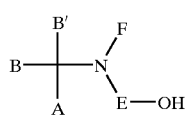

(2)

and to be used in the production method of the present invention can be produced, for example, by the method described in JP-A-61-63652 or in JP-A-01-141600.

Referring to the above general formula (1), n represents an integer of 0 to 5 and preferably is an integer of 0 to 4, more preferably an integer of 2 or 3.

The substituent A in the above general formula (1) or (2) is a phenyl group, which may be substituted, and specifically includes an unsubstituted phenyl group, a nitro-substituted phenyl group, a halo-substituted phenyl group, a phenyl group substituted by one or two lower alkoxyl groups or one or two lower alkyl groups, and the like.

The substituents B and B' in the above general formula (1) or (2) may be the same or different and each represents a phenyl group, which may be substituted, a straight or branched alkyl group containing 1 to 4 carbon atoms, or a hydrogen atom. Specifically, there may be mentioned hydrogen; lower alkyl groups such as methyl, ethyl, n-propyl, isopropyl, n-butyl, sec-butyl, isobutyl and tert-butyl; unsubstituted phenyl, nitro-substituted phenyl, phenyl substituted by one or two lower alkoxyl groups, and the like.

The substituent D in the above general formula (1) represents a straight or branched alkyl group containing 1 to 8 carbon atoms, which may be substituted, or a hydrogen atom. This alkyl group may be unsubstituted or substituted by a substituent inert to the sulfonylation reaction, for example a protected amino group such as a tertiary amino or acylamino group; a substituted carbonyl group such as a hydoxycarbonyl, alkoxycarbonyl, aminocarbonyl or acyl group; a protected hydroxyl group such as an alkyloxy or acyloxy group; an aromatic group such as a phenyl or pyridyl group; or the like.

The substituent E in the above general formula (1) represents a straight or branched alkylene group containing 1 to 8 carbon atoms, which may be substituted, and the substituent F represents a straight or branched alkyl group containing 1 to 8 carbon atoms, which may be substituted. The alkylene group and alkyl group may be unsubstituted or substituted by such a substituent inert to the sulfonylation reaction as described above.

As specific examples of the amino alcohol derivative represented by the above general formula (1) or (2), there may be mentioned N-benzyl-2-aziridinol, N-benzyl-3-azetidinol, N-benzyl-3-pyrrolidinol, N-benzyl-3-piperidinol, N-benzyl-4-piperidinol, N-benzhydryl-2-aziridinol, N-benzhydryl-3-azetidinol, N-benzhydryl-3-pyrrolidinol, N-benzhydryl-3-piperidinol, N-benzhydryl-4-piperidinol, N-trityl-2-aziridinol, N-trityl-3-azetidinol, N-trityl-3-pyrrolidinol, N-trityl-3-piperidinol, N-trityl-4-piperidinol, N-benzyl-3-methyl-2-aziridinol, N-benzyl-2-methyl-3-azetidinol, N-benzyl-4-methyl-3-pyrrolidinol, N-benzyl-4-methyl-3-piperidinol, N-benzyl-3-methyl-4-piperidinol, N-benzhydryl-3-methyl-2-aziridinol, N-benzhydryl-2-methyl-3-azetidinol, N-benzhydryl-4-methyl-3-pyrrolidinol, N-benzhydryl-4-methyl-3-piperidinol, N-benzhydryl-3-methyl-4-piperidinol, N-trityl-3-methyl-2-aziridinol, N-trityl-2-methyl-3-azetidinol, N-trityl-4-methyl-3-pyrrolidinol, N-trityl-4-methyl-3-piperidinol, N-trityl-3-methyl-4-piperidinol, N-benzyl-N-methyl-2-aminoethanol, N-benzyl-N-ethyl-2-aminoethanol, N-benzyl-N-methyl-3-aminopropanol, N-benzyl-N-ethyl-3-aminopropanol and the like. Among these, N-benzyl-3-pyrrolidinol (i.e. 1-benzyl-3-pyrrolidinol) is particularly preferred.

As specific examples of the sulfonic acid ester derivative represented by the above general formula (4) or (5) which can be produced according to the present invention, there may be mentioned N-benzyl-2-aziridinol methanesulfonate, N-benzyl-3-azetidinol methanesulfonate, N-benzyl-3- pyrrolidinol methanesulfonate, N-benzyl-3-piperidinol methanesulfonate, N-benzyl-4-piperidinol methanesulfonate, N-benzhydryl-2-aziridinol methanesulfonate, N-benzhydryl-3-azetidinol methanesulfonate, N-benzhydryl-3-pyrrolidinol methanesulfonate, N-benzhydryl-3-piperidinol methanesulfonate, N-benzhydryl-4-piperidinol methanesulfonate, N-trityl-2-aziridinol methanesulfonate, N-trityl-3-azetidinol methanesulfonate, N-trityl-3-pyrrolidinol methanesulfonate, N-trityl-3-piperidinol methanesulfonate, N-trityl-4-piperidinol methanesulfonate, N-benzyl-3-methyl-2-aziridinol methanesulfonate, N-benzyl-2-methyl-3-azetidinol methanesulfonate, N-benzyl-4-methyl-3-pyrrolidinol methanesulfonate, N-benzyl-4-methyl-3-piperidinol methanesulfonate, N-benzyl-3-methyl-4-piperidinol methanesulfonate, N-benzhydryl-3-methyl-2-aziridinol methanesulfonate, N-benzhydryl-2-methyl-3-azetidinol methanesulfonate, N-benzhydryl-4-methyl-3-pyrrolidinol methanesulfonate, N-benzhydryl-4-methyl-3-piperidinol methanesulfonate, N-bezhydryl-3-methyl-4-piperidinol methanesulfonate, N-trityl-3-methyl-2-aziridinol methanesulfonate, N-trityl-2-methyl-3-azetidinol methanesulfonate, N-trityl-4-methyl-3-pyrrolidinol methanesulfonate, N-trityl-4-methyl-3-piperidinol methanesulfonate, N-trityl-3-methyl-4-piperidinol methanesulfonate, N-benzyl-N-methyl-2-aminoethanol methanesulfonate, N-benzyl-N-ethyl-2-aminoethanol methanesulfonate, N-benzyl-N-methyl-3-aminopropanol methanesulfonate, N-benzyl-N-ethyl-3-aminopropanol methanesulfonate, N-benzyl-2-aziridinol p-toluenesulfonate, N-benzyl-3-azetidinol p-toluenesulfonate, N-benzyl-3-pyrrolidinol p-toluenesulfonate, N-benzyl-3-piperidinol p-toluenesulfonate, N-benzyl-4-piperidinol p-toluenesulfonate, N-benzhydryl-2-aziridinol p-toluenesulfonate, N-benzhydryl-3-azetidinol p-toluenesulfonate, N-benzhydryl-3-pyrrolidinol p-toluenesulfonate, N-benzhydryl-3-piperidinol p-toluenesulfonate, N-benzhydryl-4-piperidinol p-toluenesulfonate, N-trityl-2-aziridinol p-toluenesulfonate, N-trityl-3-azetidinol p-toluenesulfonate, N-trityl-3-pyrrolidinol p-toluenesulfonate, N-trityl-3-piperidinol p-toluenesulfonate, N-trityl-4-piperidinol p-toluenesulfonate, N-benzyl-3-methyl-2-aziridinol p-toluenesulfonate, N-benzyl-2-methyl-3-azetidinol p-toluenesulfonate, N-benzyl-4-methyl-3-pyrrolidinol p-toluenesulfonate, N-benzyl-4-methyl-3-piperidinol p-toluenesulfonate, N-benzyl-3-methyl-4-piperidinol p-toluenesulfonate, N-benzhydryl-3-methyl-2-aziridinol p-toluenesulfonate, N-benzhydryl-2-methyl-3-azetidinol p-toluenesulfonate, N-benzhydryl-4-methyl-3-pyrrolidinol p-toluenesulfonate, N-benzhydryl-4-methyl-3-piperidinol p-toluenesulfonate, N-benzhydryl-3-methyl-4-piperidinol p-toluenesulfonate, N-trityl-3-methyl-2-aziridinol p-toluenesulfonate, N-trityl-2-methyl-3-azetidinol p-toluenesulfonate, N-trityl-4-methyl-3-pyrrolidinol p-toluenesulfonate, N-trityl-4-methyl-3-piperidinol p-toluenesulfonate, N-trityl-3-methyl-4-piperidinol p-toluenesulfonate, N-benzyl-N-methyl-2-aminoethanol p-toluenesulfonate, N-benzyl-N-ethyl-2-aminoethanol p-toluenesulfonate, N-benzyl-N-methyl-3-aminopropanol p-toluenesulfonate, N-benzyl-N-ethyl-3-aminopropanol p-toluenesulfonate and the like.

The organic sulfonyl halide represented by the general formula (3):

wherein R represents a methanesulfonyl, ethanesulfonyl, p-toluenesulfonyl or p-nitrobenzenesulfonyl group and X represents a chlorine, bromine or iodine atom, preferably a chlorine atom, which is to be used in the production method of the present invention, comprises at least one species selected from the group consisting of methanesulfonyl chloride, ethanesulfonyl chloride, p-toluenesulfonyl chloride, p-nitrobenzenesulfonyl chloride, methanesulfonyl bromide, ethanesulfonyl bromide, p-toluenesulfonyl bromide, p-nitrobenzenesulfonyl bromide, methanesulfonyl iodide, ethanesulfonyl iodide, p-toluenesulfonyl iodide and p-nitrobenzenesulfonyl iodide. Among these, methanesulfonyl chloride is particularly preferred from the viewpoint of ready availability and reactivity.

The amount of the above organic sulfonyl halide can be selected taking into consideration the amino alcohol derivative species represented by the above general formula (1) or (2), the solvent composition to be used in carrying out the reaction, and the reaction efficiency, among others. Generally, it is used in an amount of about 1 to 10 moles relative to the amino alcohol derivative represented by the above general formula (1) or (2).

The non-water-prohibiting inorganic base to be used in the production method of the present invention is not a water-prohibiting base such as sodium hydride or sodium amide but is an inorganic base commonly and readily used as a base incapable of reacting with water but capable of occurring in the form of an aqueous solution. There may specifically be mentioned alkali metal hydroxides, carbonates and hydrogen carbonates, for example lithium hydroxide, sodium hydroxide, potassium hydroxide; lithium carbonate, sodium carbonate, potassium carbonate; lithium hydrogen carbonate, sodium hydrogen carbonate, potassium hydrogen carbonate, etc. Among these, sodium hydroxide and potassium hydroxide are preferred. These may be used singly or two or more of them may be used in combination. These inorganic bases may be added to the reaction system as they are, or mixtures prepared in advance from such inorganic bases and a reaction solvent may be used.

The above-mentioned inorganic base may be used in an amount at least to neutralize the hydrohalic acid formed in an equimolar amount as byproduct upon the reaction between the amino alcohol of general formula (1) or (2) with the organic sulfonyl halide of general formula (3) to form the sulfonic acid ester derivative of general formula (4) or (5) as well as the sulfonic acid and hydrohalic acid formed as byproducts upon hydrolysis of the organic sulfonyl halide of general formula (3) in the reaction mixture and to maintain the alkalinity of the reaction mixture, although it is not particularly restricted. Generally, the base is used in an amount of about 1 to 5 moles relative to the organic sulfonyl halide of general formula (3).

The reaction solvent to be used in the production method of the present invention is a mixed solvent composed of an aprotic organic solvent and water. The aprotic organic solvent includes, among others, hydrocarbons such as benzene, toluene and cyclohexane; ethers such as diethyl ether, tetrahydrofuran and dioxane; halogenated hydrocarbons such as methylene chloride; and like organic solvents. These may be used singly or two or more of them may be used in admixture. Among them, the use of an organic solvent capable of forming a two-phase system with the aqueous phase containing the inorganic base, for example benzene, toluene, cyclohexane, diethyl ether or methylene chloride, is preferred, and the use of toluene is particularly preferred.

The amount of the aprotic organic solvent, though not particularly restricted, may be not less than one tenth, by weight, of the amino alcohol derivative of general formula (1) or (2). Generally, the above amount is 1 to 10 times, preferably 2 to 5 times, by weight, the amount of the amino alcohol derivative of general formula (1) or (2).

The amount of water in the above-mentioned reaction solvent is preferably 0.5 to 50 times, more preferably 1 to 10 times, still more preferably 1 to 3 times, by weight, that of the above inorganic base.

In the production method of the present invention, it is preferred that the aprotic organic solvent phase and the inorganic base-containing aqueous phase form a two-phase system. By forming such system, a higher reaction yield can be obtained and the purification of the product by phase separation becomes easier as compared with the case where the aprotic organic solvent and the inorganic base-containing water form a one-phase system.

The above reaction may be carried out at a temperature within the range of from the solidifying point to the boiling point of the reaction mixture, preferably −25° C. to 60° C., more preferably −20 to 30° C., still more preferably −10 to 15° C.

Preferably, the above reaction is carried out in an inert atmosphere, such as a nitrogen atmosphere, so that side reactions such as oxidation may be suppressed as far as possible.

The above reaction is carried out in mixing the amino alcohol derivative of general formula (1) or (2) with the organic sulfonyl halide of general formula (3) in a reaction solvent composed of an aprotic organic solvent and water in the presence of a non-water-prohibiting inorganic base. Since this reaction is an exothermic one, it is generally carried out in a reactor in which the reaction mixture can be maintained under good mixing conditions and in which the reaction can be carried out while removing the heat of reaction. When the reaction is carried out batchwise in an ordinary tank reactor equipped with a stirrer, for instance, the reaction is preferably carried out either by the method comprising charging the inorganic base and the amino alcohol derivative of general formula (1) or (2) into a reaction solvent composed of an aprotic organic solvent and water, starting stirring/mixing and then gradually adding the organic sulfonyl halide of general formula (3) or by the method comprising charging the amino alcohol derivative of general formula (1) or (2) into a reaction solvent composed of an aprotic organic solvent and water, starting stirring/mixing and then gradually adding the organic sulfonyl halide of general formula (3) and the inorganic base. This reaction can also be carried out by the flow method using, for example, a tubular reactor, a multistage tank-type flow reactor, a rotary or falling thin-film reactor or the like. In this case, the reaction is preferably carried out by introducing a mixture of the amino alcohol derivative of general formula (1) or (2) and the reaction solvent, a mixture of the inorganic base and the reaction solvent and a mixture of the organic sulfonyl halide of general formula (3) and the reaction solvent concurrently into the reactor for mixing thereof within the reactor.

In any of the above-mentioned methods of carrying out the reaction, it is also possible to carry out the reaction in a multistage manner by charging a portion each of the intended amounts of the inorganic base and sulfonyl halide relative to a predetermined amounts of the amino alcohol derivative of general formula (1) or (2) and, after completion of the reaction of that part, discharging the aqueous phase and further adding water, the inorganic base and sulfonyl halide, and repeating this procedure according to need. By carrying out the reaction in such a multistage manner, it is possible to carry out the intended reaction in a reactor smaller in size as compared with the case where the reaction is carried out in a one-stage manner.

In cases where the amino alcohol derivative of general formula (1) or (2) is in an optically active form, any change in optical purity due to steric inversion, racemization or the like is not observed after carrying out the reaction according to the present invention and, thus, the sulfonyl ester derivative of general formula (4) or (5) can be obtained in an optically active form having the configuration corresponding to that of the amino alcohol derivative of general formula (1) or (2).

The final reaction mixture containing the sulfonic acid ester derivative of general formula (4) or (5) synthesized by the method of the present invention can be readily deprived of the hydrohalic acid and organic sulfonic acid formed during the reaction, the salt formed from the base charged for reaction and the excess base by a mere phase separation procedure, it is possible to very easily obtain a solution of the sulfonic acid ester derivative in the aprotic organic solvent.

This phase separation procedure for obtaining such a solution of the sulfonic acid ester derivative in the aprotic organic solvent may be combined with such a treatment procedure(s) as pH adjustment, solvent extraction or/and washing. If the precipitation of a salt, for example the salt of the hydrohalic acid or organic sulfonic acid with the inorganic base, is found in the final reaction mixture, it is also possible to dissolve the salt by adding water in an amount required for dissolving the salt to thereby facilitate the phase separation procedure. Furthermore, it is possible to combine these procedures with a solvent removing procedure to thereby obtain the sulfonic acid ester derivative as a concentrate.

Thus, for example, when 1-benzyl-3-pyrrolidinol is reacted with methanesulfonyl chloride in the presence of sodium hydroxide using a mixed solvent composed of toluene and water as the reaction solvent and the reaction mixture is obtained in the form of a two-phase system composed of a toluene phase and an aqueous phase, it is possible to obtain 1-benzyl-3-pyrrolidinol methanesulfonate as a concentrate by removing the solvent by concentrating, under reduced pressure, from the toluene solution obtained by phase separation of the reaction mixture, after or without washing the toluene phase with water.

The sulfonic acid ester derivative represented by the general formula (4) or (5) as obtained according to the present invention can be applied to the production of fine chemicals, such as medicinal compounds and agrochemicals, without any high-level purification, as mentioned hereinabove. It is also possible, however, to highly purify the derivative by further using such isolation/purification procedures as distillation, crystallization and column chromatography, employed either singly or in combination.

In the step of recovering the sulfonic acid ester derivative as a concentrate under reduced or ordinary pressure from the aprotic organic solvent solution containing the sulfonic acid ester derivative as obtained after the above-mentioned phase separation procedure, combined with such a treatment method(s) as pH adjustment, solvent extraction or/and washing, the aprotic organic solvent recovered as a distillate fraction is free of any organic base, the aprotic organic solvent for the reaction is used in the form of a mixed solvent with water according to the method of the present invention for producing sulfonic acid esters, hence can be reused as the reaction solvent in the production method of the present invention without any high-level purification procedure such as rectification or dehydration.

BEST MODES FOR CARRYING OUT THE INVENTION

The following examples illustrate the present invention in more detail. These examples are, however, by no means limitative of the scope of the invention.

EXAMPLE 1

(S)-1-Benzyl-3-pyrrolidinol (44.35 g), 132.77 g of toluene and 166.71 g of a 30% aqueous solution of NaOH were respectively weighed and placed in a 500-mL four-necked flask. While the mixture was stirred, the flask inside temperature was lowered to 6.5° C. Then, 63.14 g of methanesulfonyl chloride was added dropwise over 4 hours and 14 minutes at a flask inside temperature of 5 to 10° C. Water (35 mL) was added to dissolve the NaCl which had precipitated out in the aqueous phase, and the mixture was separated into the toluene phase and aqueous phase.

The toluene phase was concentrated using an evaporator, whereby concentrated (S)-1-benzyl-3-pyrrolidinol methanesulfonate was obtained as a pale-yellow oil in a yield of 94.8 mole percent. In the step of concentration, the toluene was recovered with a recovery rate of 95%.

EXAMPLE 2

Except that the toluene recovered in Example 1 was used as the reaction solvent without any purification procedure, the procedure of Example 1 was otherwise repeated to give concentrated (S)-1-benzyl-3-pyrrolidinol methanesulfonate as a pale-yellow oil in a yield of 94.0 mole percent.

EXAMPLE 3

N-Benzyl-N-methyl-ethanolamine (20.73 g), 61.94 g of toluene and 83.41 g of a 30% aqueous solution of NaOH were respectively weighed and placed in a 300-mL four-necked flask. While the mixture was stirred, the flask inside temperature was lowered to 6.8° C. Then, 31.68 g of methanesulfonyl chloride was added dropwise over 3 hours and 17 minutes at a flask inside temperature of 5 to 10° C. Water (33 mL) was added to dissolve the NaCl which had precipitated out in the aqueous phase, and the mixture was separated into the toluene phase and aqueous phase. A toluene solution of N-benzyl-N-methyl-ethanolamine methanesulfonate was thus obtained in a yield of 68.8 mole percent.

EXAMPLE 4

(S)-1-Benzyl-3-pyrrolidinol (44.32 g), 132.88 g of toluene and 166.95 g of a 30% aqueous solution of NaOH were respectively weighed and placed in a 500-mL four-necked flask. While the mixture was stirred, the flask inside temperature was lowered to 6.0° C. Then, 104.94 g of toluenesulfonyl chloride was added in divided portions at an interval of about 5 g/10 minutes over 3 hours and 10 minutes at a flask inside temperature of 5 to 10° C. Water (37 mL) was added to dissolve the NaCl which had precipitated out in the aqueous phase, and the mixture was separated into the toluene phase and aqueous phase. A toluene solution of (S)-1-benzyl-3-pyrrolidinol toluenesulfonate was thus obtained in a yield of 85.5 mole percent.

EXAMPLE 5

(S)-1-Benzyl-3-pyrrolidinol (22.17 g), 66.56 g of tetrahydrofuran and 83.68 g of a 30% aqueous solution of NaOH were respectively weighed and placed in a 300-mL four-necked flask. The mixture was stirred, whereupon the tetrahydrofuran phase and aqueous phase formed a two-phase system. While the above mixture was stirred, the flask inside temperature was lowered to 6.8° C. Then, 31.65 g of methanesulfonyl chloride was added dropwise over about 4 hours at a flask inside temperature of 5 to 10° C. Water (24 mL) was added to dissolve the NaCl which had precipitated out in the aqueous phase, and the mixture was separated into the tetrahydrofuran phase and aqueous phase.

The same amount of a 30% aqueous solution of NaOH as above was added to the tetrahydrofuran phase thus obtained, and the same amount of methanesulfonyl chloride as above was added dropwise to allow the reaction to proceed, under the same condition as above. The same amount of water as above was added, and the mixture was separated into the tetrahydrofuran phase and aqueous phase.

After two further repetitions of this procedure, a tetrahydrofuran solution of (S)-1-benzyl-3-pyrrolidinol methanesulfonate was obtained in a yield of 89.4%.

EXAMPLE 6

1-Benzyl-4-piperidinol (23.98 g), 168.66 g of toluene and 83.56 g of a 30% aqueous solution of NaOH were respectively weighed and placed in a 500-mL four-necked flask. While the mixture was stirred, the flask inside temperature was lowered to 6.7° C. Then, 31.73 g of methanesulfonyl chloride was added dropwise over 4 hours and 30 minutes at a flask inside temperature of 5 to 10° C. Water (33 mL) was added to dissolve the NaCl which had precipitated out in the aqueous phase, and the mixture was separated into the toluene phase and aqueous phase. A toluene solution of 1-benzyl-4-piperidinol methanesulfonate was thus obtained in a yield of 40.3 mole percent.

INDUSTRIAL APPLICABILITY

The present invention, which has the constitution mentioned above, makes it possible to prepare sulfonic acid ester derivatives represented by the above general formula (4) or (5) from the amino alcohol derivatives represented by the above general formula (1) or (2) in a simple, easy, safe and economical manner while reducing the load on the environment.

What is claimed is:

1. A method of producing a sulfonic acid ester derivative represented by the general formula (4):

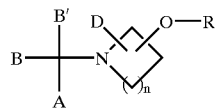

wherein n is 2, A represents a phenyl group, which may be substituted, B and B' are the same or different and each represents a phenyl group, which may be substituted, a straight or branched alkyl group containing 1 to 4 carbon atoms or a hydrogen atom, D represents a straight or branched alkyl group containing 1 to 8 carbon atoms, which may be substituted, or a hydrogen atom and R represents a methanesulfonyl, ethanesulfonyl, p-toluenesulfonyl or p-nitrobenzenesulfonyl group, which comprises reacting an amino alcohol derivative represented by the general formula (1):

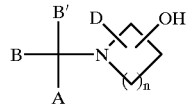

wherein n, A, B, B' and D are as defined above, with an organic sulfonyl halide represented by the general formula (3):

wherein R is as defined above and X represents a chlorine, bromine or iodine atom, in a mixed solvent composed of an aprotic organic solvent and water in the presence of a non-water-prohibiting inorganic base.

2. The production method according to claim 1, wherein the aprotic organic solvent phase and the aqueous phase containing the non-water-prohibiting inorganic base form a two-phase system.

3. The production method according to claim 1, wherein the amino alcohol derivative represented by the general formula (1) is in an optically active form and the sulfonic acid ester derivative represented by the general formula (4) is in an optically active form.

4. The production method according to claim 1, wherein the aprotic organic solvent is toluene.

5. The production method according to claim 1, wherein the non-water-prohibiting inorganic base comprises at least one species selected from the group consisting of lithium hydroxide, sodium hydroxide, potassium hydroxide, lithium carbonate, sodium carbonate, potassium carbonate, lithium hydrogen carbonate, sodium hydrogen carbonate and potassium hydrogen carbonate.

6. The production method according to claim 5, wherein the non-water-prohibiting inorganic base comprises at least one species selected from among sodium hydroxide and potassium hydroxide.

7. The production method according to claim 1, wherein the organic sulfonyl halide represented by the general formula (3) is methanesulfonyl chloride.

8. The production method according to claim 1, wherein the amino alcohol derivative represented by the general formula (1) is 1-benzyl-3-pyrrolidinol.

9. The production method according to claim 2, wherein the amino alcohol derivative represented by the general formula (1) is in an optically active form and the sulfonic acid ester derivative represented by the general formula (4) is in an optically active form.

10. The production method according to claim 9, wherein the aprotic organic solvent is toluene.

11. The production method according to claim 2, wherein the aprotic organic solvent is toluene.

12. The production method according to claim 2, wherein the non-water-prohibiting inorganic base comprises at least one species selected from the group consisting of lithium hydroxide, sodium hydroxide, potassium hydroxide, lithium carbonate, sodium carbonate, potassium carbonate, lithium hydrogen carbonate, sodium hydrogen carbonate and potassium hydrogen carbonate.

13. The production method according to claim 3, wherein the non-water-prohibiting inorganic base comprises at least one species selected from the group consisting of lithium hydroxide, sodium hydroxide, potassium hydroxide, lithium carbonate, sodium carbonate, potassium carbonate, lithium hydrogen carbonate, sodium hydrogen carbonate and potassium hydrogen carbonate.

14. The production method according to claim 4, wherein the non-water-prohibiting inorganic base comprises at least one species selected from the group consisting of lithium hydroxide, sodium hydroxide, potassium hydroxide, lithium carbonate, sodium carbonate, potassium carbonate, lithium hydrogen carbonate, sodium hydrogen carbonate and potassium hydrogen carbonate.

15. The production method according to claim 2, wherein the organic sulfonyl halide represented by the general formula (3) is methanesulfonyl chloride.

16. The production method according to claim 3, wherein the organic sulfonyl halide represented by the general formula (3) is methanesulfonyl chloride.

17. The production method according to claim 4, wherein the organic sulfonyl halide represented by the general formula (3) is methanesulfonyl chloride.

18. The production method according to claim 5, wherein the organic sulfonyl halide represented by the general formula (3) is methanesulfonyl chloride.

19. The production method according to claim 6, wherein the organic sulfonyl halide represented by the general formula (3) is methanesulfonyl chloride.

20. The production method according to claim 2, wherein the amino alcohol derivative represented by the general formula (1) is 1-benzyl-3-pyrrolidinol.

21. The production method according to claim 3, wherein the amino alcohol derivative represented by the general formula (1) is 1-benzyl-3-pyrrolidinol.

22. The production method according to claim 4, wherein the amino alcohol derivative represented by the general formula (1) is 1-benzyl-3-pyrrolidinol.

23. The production method according to claim 5, wherein the amino alcohol derivative represented by the general formula (1) is 1-benzyl-3-pyrrolidinol.

24. The production method according to claim 6, wherein the amino alcohol derivative represented by the general formula (1) is 1-benzyl-3-pyrrolidinol.

25. The production method according to claim 7, wherein the amino alcohol derivative represented by the general formula (1) is 1-benzyl-3-pyrrolidinol.

* * * * *

UNITED STATES PATENT AND TRADEMARK OFFICE
CERTIFICATE OF CORRECTION

PATENT NO. : 6,794,519 B2
DATED : September 21, 2004
INVENTOR(S) : Fumihiko Kano et al.

It is certified that error appears in the above-identified patent and that said Letters Patent is hereby corrected as shown below:

<u>Title page,</u>
After "[22] Filed: Feb. 8, 2002" insert the following:
-- Related U.S. Application Data
[63] Continuation of application No. PCT/JP00/08277, 24 Nov. 2000 --; and
-- [30] Foreign Application Priority Data
June 8, 2000    (JP)    Japan …………….. 2000-172509 --

Signed and Sealed this

Twenty-first Day of December, 2004

JON W. DUDAS
*Director of the United States Patent and Trademark Office*